United States Patent
Régnier et al.

(10) Patent No.: US 9,555,236 B2
(45) Date of Patent: Jan. 31, 2017

(54) IMPLANTABLE CAPSULE FOR LEADLESS CARDIAC PACING (71) Applicant: SORIN CRM SAS, Clamart (FR)

(72) Inventors: Willy Régnier, Longjumeau (FR); Philippe D'hiver, Châtillon (FR); Jean-François Ollivier, Gif sur Yvette (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/744,916

(22) Filed: Jun. 19, 2015

(65) Prior Publication Data
US 2016/0008594 A1    Jan. 14, 2016

(30) Foreign Application Priority Data
Jun. 25, 2014    (FR) ..................... 14 55896

(51) Int. Cl.
| A61N 1/375 | (2006.01) |
| A61N 1/05 | (2006.01) |
| B23K 26/22 | (2006.01) |
| B23P 19/04 | (2006.01) |

(52) U.S. Cl.
CPC ........... *A61N 1/0575* (2013.01); *A61N 1/3756* (2013.01); *B23K 26/22* (2013.01); *B23P 19/04* (2013.01)

(58) Field of Classification Search
CPC .... A61N 1/0575; A61N 1/3756; B23K 26/22; B23P 19/04
USPC ............ 607/2, 116, 119, 120, 126, 127, 131
See application file for complete search history.

(56) References Cited

U.S. PATENT DOCUMENTS

| 5,456,708 | A | * | 10/1995 | Doan | ................... | A61N 1/0573 607/127 |
| 2005/0149157 | A1 | * | 7/2005 | Hunter | ................... | A61K 38/17 607/119 |
| 2008/0109042 | A1 | * | 5/2008 | Bodner | ............... | A61N 1/0573 607/9 |
| 2012/0330392 | A1 | * | 12/2012 | Regnier | ................ | A61N 1/059 607/119 |
| 2013/0123872 | A1 | * | 5/2013 | Bornzin | ............ | A61N 1/36592 607/17 |

FOREIGN PATENT DOCUMENTS

| EP | 2 394 695 | 12/2011 |
| WO | WO-01/26706 | 4/2001 |
| WO | WO-2012/051235 | 4/2012 |

OTHER PUBLICATIONS

Preliminary Search Report for French Patent Application No. FR 1455896, dated Feb. 18, 2015, 1 page.

* cited by examiner

*Primary Examiner* — Edward Moran
*Assistant Examiner* — Michael Carey
(74) *Attorney, Agent, or Firm* — Foley & Lardner LLP (57) ABSTRACT

The invention relates to an implantable capsule, particularly an autonomous capsule of cardiac stimulation, including a tubular body provided at the distal end of an anchoring element with a helical screw adapted to penetrate tissue a wall of an organ of a patient, the body housing a set of functional elements of the capsule. It includes, in an annular area surrounding the base of the screw recessed arrangements defining a set of flush tips oriented in a circumferential direction opposite to that of the screwing, to avoid the unscrewing of the capsule.

20 Claims, 5 Drawing Sheets

IMPLANTABLE CAPSULE FOR LEADLESS CARDIAC PACING

CROSS-REFERENCE TO RELATED PATENT APPLICATIONS

This application claims the benefit of and priority to French Patent Application No. 1455896, filed Jun. 25, 2014, which is incorporated herein by reference in its entirety.

BACKGROUND

The invention relates to "active implantable medical devices" as defined by Directive 90/385/EEC of 20 Jun. 1990 of the Council of the European Communities, specifically to devices that continuously monitor heart rhythm and deliver to the heart if necessary stimulation, resynchronization and/or defibrillation pulses in cases of arrhythmia detected by the device.

The invention relates especially, but is not limited to, those devices that are in the form of an autonomous capsule intended to be implanted in a heart chamber (atrium or ventricle, right or left). These capsules are free of any mechanical connection to an implantable (such as a housing of the stimulation pulse generator) or non-implantable (external device such as programmer or monitoring device for patient remote monitoring) main device. For this reason they are called "leadless capsules" to distinguish them from electrodes or sensors disposed at the distal end of a conventional probe (lead), which is traversed throughout its length by one or more conductors connecting the electrode or sensor to a generator connected to an opposite, proximal end of the lead.

EP 2394695 A1 (Sorin CRM), now EP 2394695 B1, describes an autonomous intracardiac capsule, and a method to implant it to the selected detection/stimulation site and reposition it if necessary.

Note, however, as will be understood by reading the description, that the autonomous nature of the capsule is not inherently a necessary feature of the invention, and that the latter can be both applied to capsules permanently mounted at the distal end of a lead.

An implantable capsule includes a body housing the main components of the device (electronic circuits, power source, stimulation electrodes, etc.) and a base secured to the body and rigidly supporting methods for fixing to the wall.

In the case of cardiac leads, two types of fasteners are known and conventionally employed: fixation with "barbs" is the oldest and is still used marginally, but the leads based on a fixing screw have supplanted barb leads and currently represent the majority of the market. They allow a generally robust and effective fixation.

The screw is a projecting helical screw extending axially the capsule body and adapted to penetrate the heart tissue by screwing in the implantation site, in the same method as the conventional screw leads.

However, the fixing of such devices is still a critical point to the extent that accidental detachment of the capsule would cause the latter to be released into the heart chamber and then transported by the blood in the venous or arterial system. Complication risk to the patient would be extremely high, as well as the risk of cardiac system injury which can be generated by the end of the fastening system or other projecting regions of the implant such as a needle electrode or a projecting ridge.

More than a lead device, an autonomous device undergoes stresses and movements generated by the heart wall, as it does not benefit from the axial holding force from the lead body.

To fulfill its permanent anchoring function, the fastening system must also include a function of irreversibility. That is to say it can be removed from the heart wall only by the doctor's voluntary action and according to a predefined method, but in no case by repeated movements or vibrations of the heart, or by modification of heart muscle due to the disease or tissue aging.

WO 2012/051235 A1 discloses reverse rotation prevention methods which implement arrangements with protruding spikes formed directly on the screw and oriented in an opposite circumferential direction to the direction of screwing, or protruding spikes penetrating the tissues at the base of the screw. This implies significant damage to all tissues crossed or adjacent during implantation of the implant.

SUMMARY

One aspect of the present invention provides an autonomous implantable device which allows ensuring good opposition to unscrewing while having a much smaller traumatic effect.

This is particularly important to the extent that surrounding tissues are the primary targets of the stimulation method, and it is important to protect these tissues during implantation and during operation of the device, to ensure low pacing thresholds and thus preserve the longevity of the device.

More specifically, one embodiment of the invention proposes to this purpose an implantable capsule, including a cardiac stimulation autonomous capsule, including in a manner known per se a tubular body provided at its distal end with a helical anchoring screw member capable of penetrating into a tissue of a wall of an organ of a patient, the body housing a set of functional elements of the capsule. The capsule further includes a set of flush peaks oriented in a circumferential direction opposite to that of the screwing.

In one embodiment of the invention, the capsule includes an annular support surface formed in an annular region surrounding the base of the screw in the radial direction; and formed in a flush manner in said annular support surface, hollowed recesses defining said set of peaks.

According to various advantageous embodiments:
  The hollowed recesses include oblique recesses formed from a generally continuous annular face of the support so as to form peaks pointing in an opposite circumferential direction to the screwing, in particular with an inclination angle between the recesses between 40° and 60° relative to the surface of the annular face;
  The proportion of the surface of the annular face occupied by the recesses is between 20 and 40%, and preferably close to 30%;
  The screw anchoring member is formed from a resilient metal wire wound in a helix and terminating in a peak, and able to generate a traction force of said annular region toward said wall, namely with a spacing between the successive turns of the helix which increases between a base of the screw and its tip;
  The capsule further includes a tip electrode projecting inside the screw member, this electrode being configured as a harpoon. The electrode may in particular be a revolution part centered on the axis rotation of the capsule during screwing, and/or include a conical head at the free end of a stem narrower than the head;

The capsule further includes a pharmaceutical product diffusion ring disposed within the annular region, the recesses being adapted to facilitate the circulation of the product towards the outside of said region;

The capsule includes a piece of biodegradable material wherein the hollowed recesses defining the set of peaks are formed, the biodegradable material being especially possibly a bioabsorbable biopolymer of the group consisting of: polylactides (PLA), polyglycolides (PGA) and polylactide-co glycolide (PLGA).

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the device of the invention will now be described, along with examples of realization of an implantable capsule.

Figure 1:
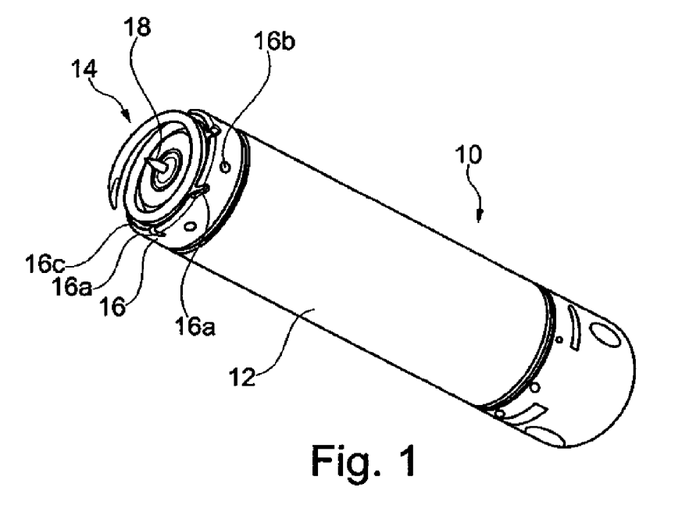
FIG. 1 is an overall perspective view of an implantable capsule according to one embodiment of the invention.

Referring firstly to FIG. 1, an implantable capsule 10 is shown, here an autonomous capsule for cardiac stimulation, including a capsule body 12 and an anchoring member of helical screw-type 14.

The screw 14 is formed by a helically wound wire with a right screw pitch and is mounted on a screw support 16 incorporating arrangements ensuring the irreversibility of the anchoring as will be seen hereinafter.

The screw 14 is rendered permanently secured to its support 16, for example by laser welding according to the distributed welding points.

The assembly is then permanently secured to the body of the capsule 12 by a laser welding bead.

Note that the material of the screw 14 and of its support 16 may be different, for example a platinum/iridium 90/10 couple for the screw 14, and titanium for the support 16. It is indeed possible, as will be seen below with reference to the embodiment shown in FIGS. 8 and 9, to implement an effective method of assembly of these elements even if they are made of heterogeneous materials.

The various parts are made, for example, of biocompatible metal alloys such as stainless steel or a titanium alloy, preferably a biocompatible titanium alloy for the capsule body 12 and the support 16.

The arrangements for the irreversibility of fastening include notches or recesses 16a formed in the support 16.

The fastener assembly consisting of parts 14, 16 has a diameter preferably equal to that of the body of the implant, typically 6 to 7 mm, and a slightly lower axial length, typically between 4 and 6 mm. The screw 14 defines a space occupied by another sub-assembly of the device, here a sub-assembly of stimulation electrodes.

The fastening system is designed to secure the implant in a stable and a sustainable manner over time through the helical screw 14 forming a spring with scalable turns and ending in a point capable of puncturing the endothelium and of penetrating muscle tissue. This presses the cardiac wall on the generally annular end face of the support 16, substantially at the same position (in the axial direction) than the inner bearing surface of the electrode system.

In more detail, the screw support 16 presents on said end face 16c a series of recesses 16a which perform the function of irreversibility once in contact with the endothelium. In this position, the fastening system is unremovable. Under the action of the screw 14 which acts as a tension spring carrying an axial retaining force, the cardiac wall is pressed against the face 16c of the screw support 16 and locally anchors in the recesses (here six in number, uniformly distributed) by the above-mentioned spring effect.

As will be discussed in more detail later, the six recesses may be defined as sharp, but shallow edges in their (circumferentially) area opposite the direction of screwing of the helix and then provide six punctual anchoring points distributed on the endothelium (mutual spacing of 60° in this example), which provide the irreversibility of screwing to anchor the capsule.

Figure 2:
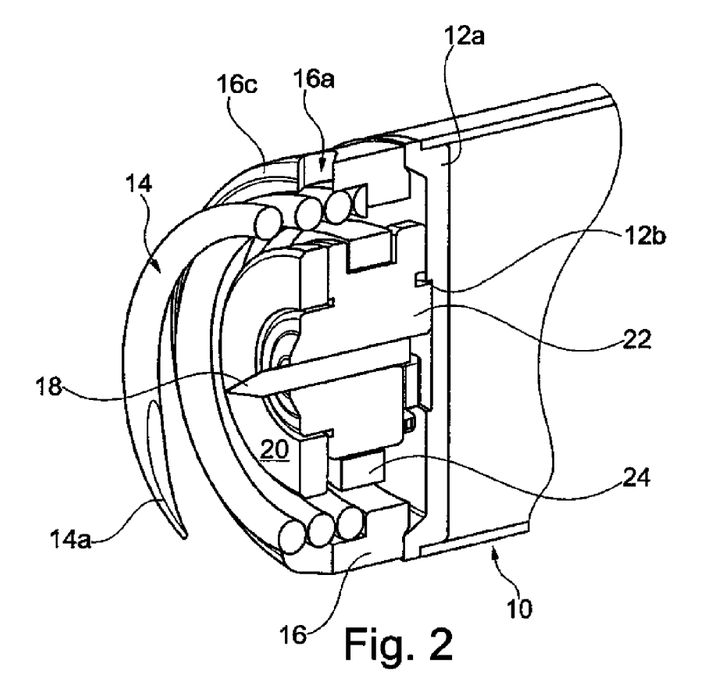
FIG. 2 is a perspective view and in half-section of a distal region of the capsule of FIG. 1.

Now in more detail and with reference to FIG. 2, a stimulation subassembly is observed, constituted by two electrodes 18 and 20 maintained by an electrode support 22 which also supports at its periphery a ring 24 for elution of a steroid product.

The support 22 is positioned coaxially with the screw support 16, inside the latter, and fixed by adhesive or other suitable methods on a wall 12a closing the interior of the capsule body 12 at its distal, screw side, end, the support being accurately located thanks to a circular shoulder 12b provided on the outer face of said wall.

The central pacing tip electrode 18 is fixed (by crimping, bonding, etc.) in the center of the support 22 and electrically connected to the internal electronics of the capsule accommodated in the body 12 via a micro-feedthrough. The second electrode 20 here has the form of a washer positioned and fixed, for example by bonding, on the external face of the support 22 and is also connected through a micro-feedthrough to the internal electronics.

The ring 24 is impregnated with a steroid such as dexamethasone and is positioned under the electrode 20. The steroid product can reduce tissue inflammation during the first weeks after implantation.

The electronics associated with the electrodes can implement, in the case of cardiac pacing, functions of sensing and pacing, the described structure ensuring a reliable and permanent contact between the electrodes 18, 20 and the tissues.

The helix screw 14 is constituted of a metal wire with a diameter of about 0.5 mm, with a winding diameter typically about 5 mm and preferably identical to the body 12 of the device. The screw includes a planar base followed by two adjacent turns and a final turn extending, e.g., approximately on 1.5 turns with an inter-coil space of the same order of magnitude as the diameter of the wire.

The free end of the screw 14 is refined, in this case by machining in two mutually orthogonal planes, creating a perforating, but not sharp tip 14a. The purpose of this tip is to allow crossing the endothelium and then of easily penetrating into the cardiac muscle, while creating minimal tissue damage. The helix screw 14 here is made of implantable and biocompatible stainless steel 316L or of any other equivalent material, which delivers a stiffness of about 0.1 N/mm (linear spring stiffness, as measured by tensile or compression using a dynamometer on a 1 mm stroke).

This gives the screw an axial flexibility which gives it a spring effect, operating a tensile effort to maintain firm contact between the support 16 and the cardiac wall. Thus, during the penetration of the screw 14 in the muscle, the screw deforms axially until contact with the free edge 16c of the support 16 with the endothelium. The spring effect of the screw will then axially compress the endothelium and the muscle between the coils and create a wedging effect. In addition, the close proximity of the coils and their tensile effect on the endothelium force the input thereof in the anti-unscrewing notches. During this movement, the pacing tip electrode 18 pierces the endothelium and thus comes into contact with the excitable cells of the cardiac wall.

Other coil configurations are of course possible, but it is advantageous to provide a spacing between turns which increases from the base of the screw (wherein as we saw the spacing may be zero) and the tip 14a of the screw. This helps promote the axial tensile force applying the support 16 against the cardiac wall.

Furthermore it is understood that the electrode 18 contributes to the fastening of the capsule while providing reliable and continuous contact with the compressed tissues by the axial force of the screw 14 towards the support 16.

Such a configuration is particularly suitable for low energy stimulation, with a needle length of the order of 1.2 mm and a diameter of the order of 0.4 mm, a surface area of the order of 1 mm².

Figure 3:
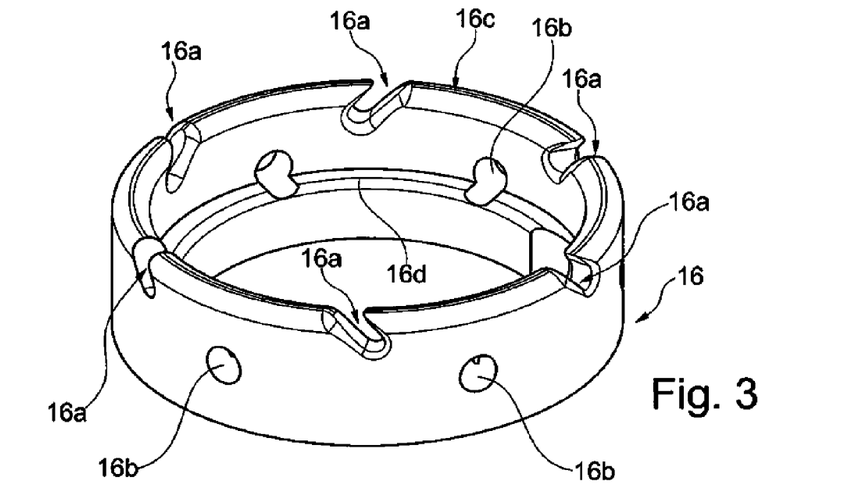
FIG. 3 is a perspective view of an anchoring screw support of the capsule of FIGS. 1 and 2.
Figure 4:
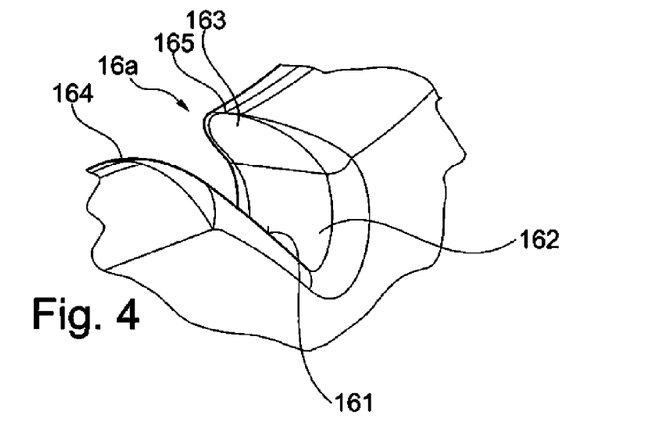
FIG. 4 is a perspective view of a detail of the support of FIG. 3.
Figure 5:
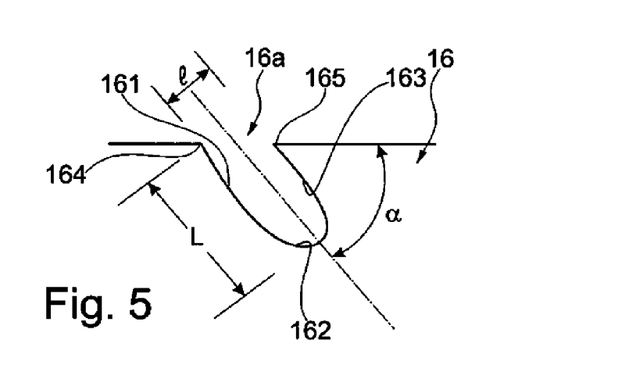
FIG. 5 is a side view of the detail of FIG. 4.

Referring particularly to FIGS. 3-5, the support 16 of the screw 14 has as stated a face or support edge 16c, preferably with a slightly rounded profile, from which six recesses 16a for performing six sharp edges 165, highly localized and highly punctual (see in particular FIGS. 4 and 5) ensuring the irreversibility of the screwing of the capsule made as described above, are formed in an oblique direction.

Localized perforation of endothelium is achieved by the sharp edges 165, the other edges which form the boundaries of the notch being deliberately very rounded so as not to spread or enlarge the piercing of the endothelium during the unscrewing effort. The support surface supporting unscrewing constraints being maximized, the risks of tearing of the endothelium are minimized.

Preferably, but not limited to, the relative surface area occupied by the recesses of the support surface 16c is from 20 to 40% of this surface, more preferably around 30%, which allows to limit the traumatic effect of the sharp edges 165 by limiting the penetration of tissues into the recesses 16a, while ensuring a good attachment of said edges 165 in the endothelium, and thus the effectiveness of the anti-unscrewing function.

The dimensions of the recesses may vary. For example and with reference particularly to FIG. 5, the width l may be of the order of 0.3 to 0.8 mm, the depth or the length L can be between 0.5 and 1 mm, and their inclination a may be between 20 and 60°, and preferably close to 45°.

In an advantageous implementation variant, the recesses 16a defining the sharp edges 165 are realized in a biodegradable insert on the support 16. The material used to make this patch may especially be a bioabsorbable biopolymer such as polylactide (PLA), polyglycolide (PGA) and polylactide-co-glycolide (PLGA) or any other equivalent, implantable, absorbable material in body. The anti-unscrewing function is then provided for a predetermined period, for example from 3 to 12 months, during which the fibrosis progressively overlap the base of the capsule. Then, in the long term it will become easier to remove the capsule once the anti-unscrewing function has disappeared.

Figure 6:
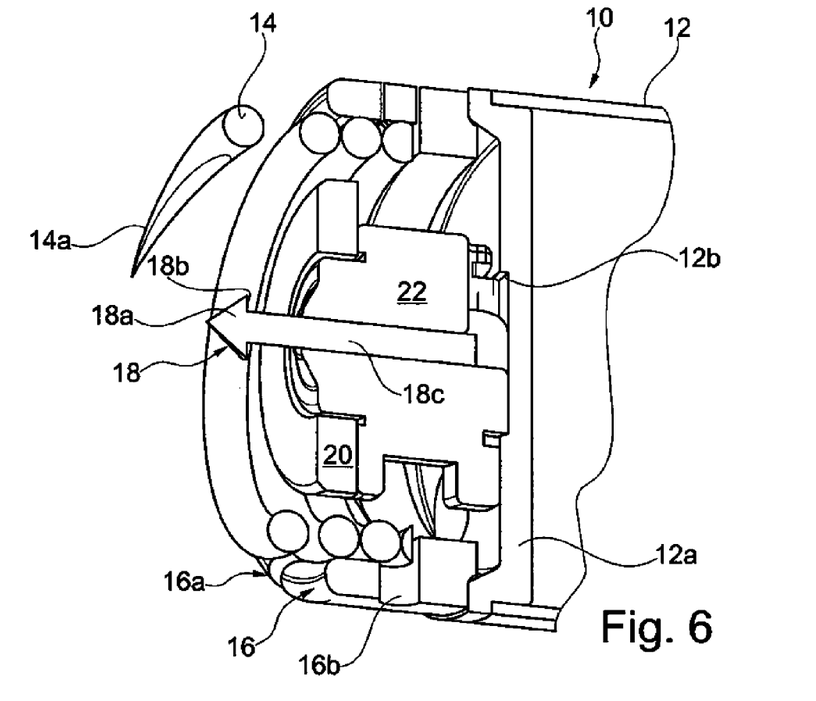
FIG. 6 is a perspective view and in half-section of a distal region of a capsule incorporating an alternative embodiment.
Figure 7:
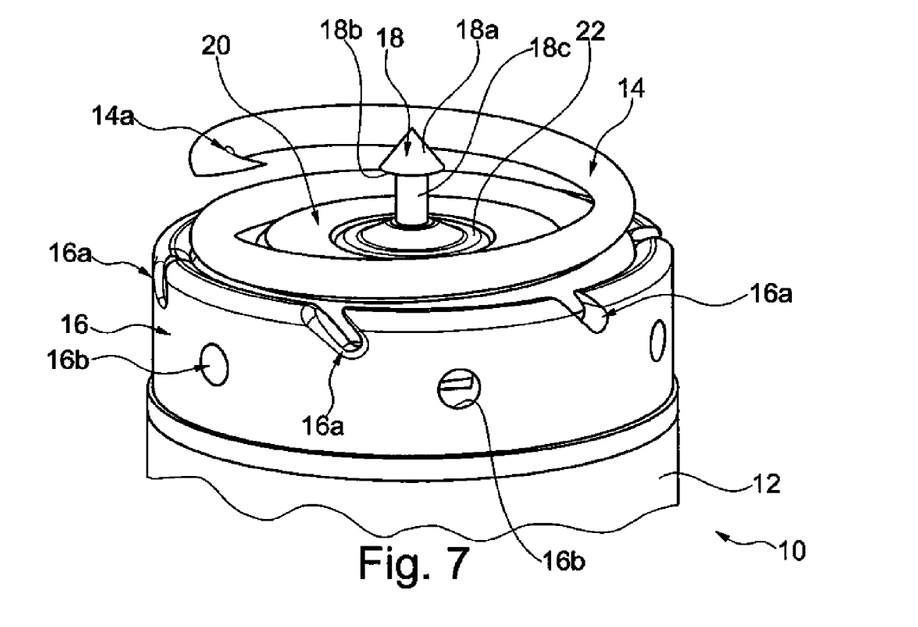
FIG. 7 is a perspective view, in another direction, of that distal region.

Referring now to FIGS. 6 and 7, we will describe an alternative embodiment of the tip electrode 18. The latter in this case has an enlarged head 18a, preferably of conical shape, joining at its base, an annular returning shoulder 18b, a narrower rod 18c.

The shoulder 18b has a surface which mechanically strengthens the stability of the capsule on the cardiac wall, participating in the retention of the tissue compressed by the axial force of the screw 14.

In this example, the shoulder 18b has a ring width of the order of 0.2 mm. This value can vary depending on requirements and the size of the capsule, typically between 0.05 and 1 mm.

The cone angle is in turn included between about 30 and 60°, and typically around 50°.

A permanent assembly solution of the screw 14 on its support 16 will now be described, this solution being implemented independently of the anti-unscrewing and attachment characteristics to the cardiac wall, as detailed in the foregoing.

The problem solved by this solution is to assemble a screw 14 made of stainless steel or of other not directly sealable material on the titanium housing of the capsule.

Figure 8:
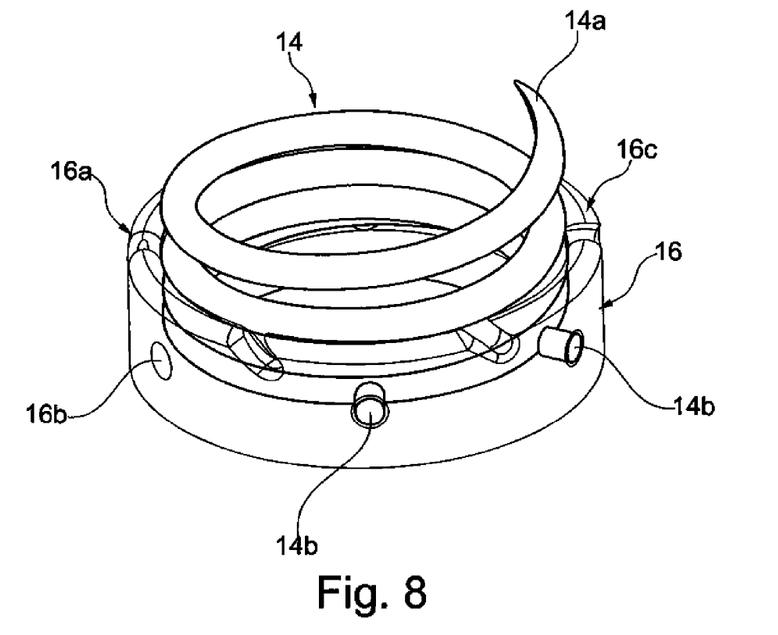
FIG. 8 is a perspective view of a screw-support assembly according to another aspect of an implantable capsule, the screw being visible in transparency.
Figure 9:
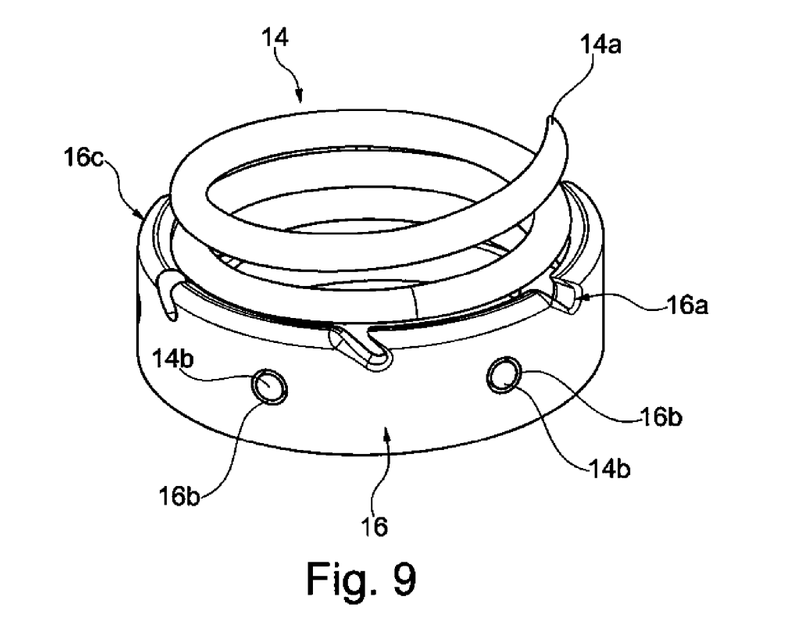
FIG. 9 is a perspective view of the screw-support assembly of FIG. 8.

Thus, referring to FIGS. 8 and 9, the support 16 has a configuration including a plurality of through orifices 16b, having a cross section approximately corresponding to that of the rods or tubes and for example circular, formed in the wall of the support 16. These orifices receive counterpart rods or tubes 14b formed on the periphery of the base of the screw 14, corresponding angular locations. In this example, two through orifices 16b, spaced for example by 60°, and two corresponding tubes or rods 14b, are provided.

Specifically, first, the screw 14 slides under slight tightening into the support 16 until the axial abutment against a shoulder formed in the central bore of the support. Several radial through holes 16b are arranged in the support 16, which coincide with the part of the screw with contiguous coil. A rod or a tube 14b of the same material as the screw, or a laser-weldable material to the screw material, is then inserted into each of these side holes. In the (preferred) case of a tube, the bore of the tubes then leads to the turns of the screw. A laser shot through these holes then allows direct tube/screw welding ensuring the requirements of a good laser welding, namely: i) material compatibility, ii) direct contact and iii) visual access for shooting and quality control.

This welding being done, the screw is locked in translation and rotation in its support by mechanical anchoring and without direct laser welding, which leaves a lot of freedom in the combination of support/screw materials.

Other significant advantages of this solution are the small footprint and very low complexity of machining.

Figure 10:
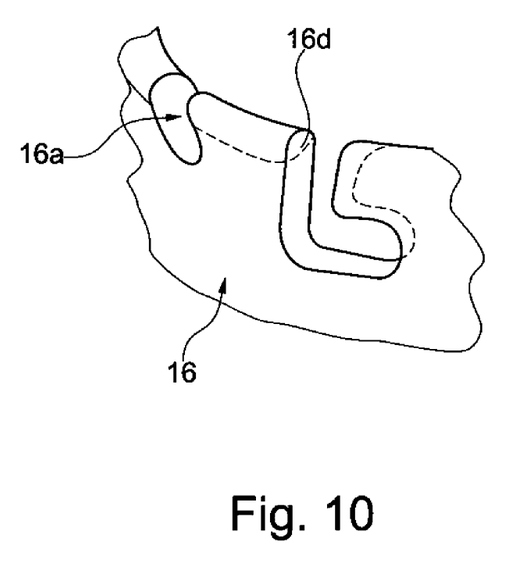
FIG. 10 is a partial perspective view of an alternative embodiment of the support for fixing the screw on the support.

According to an alternative embodiment illustrated in FIG. 10 of the drawings, a bayonet-type mounting may be provided between the screw 14 and its support 16, the screw 14 then having at its base two rods or tubes such as 14b, preferably diametrically opposed, and the support 16 having in two diametrically opposite regions notches 16d in the general form of a L extending from the free face of the support 16. This allows, prior to laser welding, the mounting of the screw 14 by axial translation for engagement of the rods or tubes in the notches, followed by a rotation for the locking of the rods or tubes at the bottom of the notches.

It can exist, in addition to these two notches, other notches 16d and/or other circular holes 16b.

In the first case described above, the assembly method of the capsule preferably includes the steps of:

a) fixing the support 16 to the body by welding,
b) engaging the base of member 14 within said support,
c) engaging the rods or tubes 14b in the orifices 16b,
d) welding the rods or tubes on the base of member 14, by laser welding through the inside of the support, and
e) welding the rods or tubes in their respective orifices, by laser welding, externally to the support.

Note that the "welding" step d) should not be understood in the narrow sense of mechanical welding with melting of the material of two separate pieces, but as an operation to collapse the material of the rod or of the tube within the housing supporting the mechanical connections and to enhance the atraumatic function by removal of the protruding shapes.

In the case of the variant of FIG. 10, the method preferably includes the steps of:

a) fixing the support 16 provided with notches 16d to the body by welding,
b) welding the rods or tubes on the base of member 14 by laser welding,
c) pre-assembling the anchoring element with its base in the support, by bayonet-type mounting involving said rods or tubes and the said notches, and
d) welding the rods or tubes in the notches, by laser welding, externally to the support.

Advantageously, orifices 16b or 16d in a greater number to the number of rods or tubes 14b of the screw 14 are present. In this method, the orifices 16b or 16d remaining free facilitate the diffusion of the steroid product delivered by the ring 24 radially towards the cardiac wall.

In another variant, it is planned that the notches 16d for such a bayonet type mounting are formed to participate in an anti-unscrewing function as described above.

The various components and parts described above may be made by machining or other shaping in accordance with conventional techniques.

Moreover, it is planned as described above that the support 16 surrounds the base of the anchoring element, but alternatively that the base of the anchoring member surrounds the support, in which case a skilled-in-the-art person will make necessary modifications, in particular with regard to the positioning of rods or tubes 14b for fixing between the anchoring element and support.

The capsule can be placed by the practitioner according to the method described in particular in EP 2394695 A1, now EP 2394695 B1, and also extracted using a known technique, the proximal portion 12 of the body of the capsule being arranged in an appropriate method.

The invention is not limited to the attachment of an autonomous stimulation capsule in a cardiac wall of the human body, but can be implemented in other implantable systems, whether they are autonomous or contained in a lead tip. Depending on the nature of the attachment wall in question, the lengths of the helix and optionally of the electrode can be easily adapted by a skilled in the art person, without degrading the fixing and irreversibility performances.

What is claimed is:

1. An implantable capsule for cardiac pacing, comprising:
a capsule body;
a helical screw coupled to an end of the capsule body, the helical screw adapted to penetrate into a tissue when rotated in a screwing direction;
an annular support surface formed in an annular region surrounding a base of the helical screw and located outside of the helical screw in radial direction; and
a plurality of hollowed recesses formed in the annular support surface and defining a plurality of peaks, the peaks oriented in a circumferential direction opposite that of the screwing direction.

2. The capsule of claim 1, wherein the hollowed recesses comprise oblique recesses formed in the annular support surface.

3. The capsule of claim 2, wherein the recesses have an angle of inclination between 40° and 60° relative to the annular support surface.

4. The capsule of claim 1, wherein the proportion of the area of the annular support surface occupied by the recesses is between 20% and 40%.

5. The capsule of claim 1, wherein the helical screw is formed from a resilient wire helically wound and terminating in a peak and adapted to generate a traction force of the annular region in the direction of the wall.

6. The capsule of claim 5, wherein the spacing between successive turns of the helical screw increases between the base of the helical screw and its tip.

7. The capsule of claim 1, further comprising a tip electrode projecting inside the helical screw.

8. The capsule of claim 7, wherein the electrode is a revolution part centered on a rotation axis of the capsule during screwing.

9. The capsule of claim 8, wherein the electrode includes a conical head at a free end of a rod that is narrower than the conical head.

10. The capsule of claim 1, further comprising a drug eluting ring disposed within the annular region, the recesses being adapted to promote circulation of a drug towards the outside of that region.

11. The capsule of claim 1, wherein the plurality of peaks are formed from a biodegradable material.

12. The capsule of claim 11, wherein the biodegradable material is a bioabsorbable biopolymer of the group consisting of: polylactides (PLA), polyglycolides (PGA) and polylactide-co-glycolides (PLGA).

13. A method of assembling an implantable capsule for cardiac pacing, the implantable capsule comprising a capsule body, a helical screw coupled to an end of the capsule body, the helical screw including a rod extending therefrom, an annular support, and a plurality of hollowed recesses formed in a surface of the annular support, the method comprising:
sliding the helical screw into the annular support until the helical screw axially abuts against a shoulder in the central bore of the annular support;
inserting the rod into a radial through hole in the annular support;
welding the rod and helical screw together via a laser welding process; and wherein the helical screw is adapted to penetrate into a tissue of a wall an organ of a patient when rotated in a screwing direction.

14. The method of claim 13, wherein the rod is made of the same material as the helical screw or a material that is laser-weldable to the helical screw.

15. The method of claim 13, wherein a plurality of rods extend from the helical screw and wherein the rods are formed on the periphery of the base of the helical screw; and
   wherein a plurality of radial through holes are formed in the wall of the annular support and configured to receive the rods at corresponding angular locations.

16. The method of claim 15, wherein the radial through holes are spaced 60° apart.

17. The method of claim 15, wherein the rods are hollow such that the rods are tubes.

18. The method of claim 13, wherein the plurality of hollowed recesses define a plurality of peaks, the peaks oriented in a circumferential direction opposite that of the screwing direction.

19. The method of claim 18, wherein the helical screw is formed from a resilient wire helically wound and terminating in a peak and adapted to generate a traction force of the annular region in the direction of the wall.

20. The capsule of claim 18, wherein the spacing between successive turns of the helical screw increases between the base of the helical screw and its tip.

* * * * *